US011653875B2

(12) United States Patent
Hanssen

(10) Patent No.: US 11,653,875 B2
(45) Date of Patent: May 23, 2023

(54) METHOD FOR DETERMINING AND VISUALIZING TOOTH POSITIONS UNDER THE ACTION OF BITING FORCES

(71) Applicant: SICAT GMBH & CO. KG, Bonn (DE)

(72) Inventor: Nils Hanssen, Bonn (DE)

(73) Assignee: SICAT GMBH & CO. KG, Bonn (DE)

( * ) Notice: Subject to any disclaimer, the term of this patent is extended or adjusted under 35 U.S.C. 154(b) by 9 days.

(21) Appl. No.: 16/756,845

(22) PCT Filed: Oct. 16, 2018

(86) PCT No.: PCT/EP2018/078231
§ 371 (c)(1),
(2) Date: Apr. 17, 2020

(87) PCT Pub. No.: WO2019/076888
PCT Pub. Date: Apr. 25, 2019

(65) Prior Publication Data
US 2020/0237289 A1 Jul. 30, 2020

(30) Foreign Application Priority Data
Oct. 20, 2017 (DE) .................. 10 2017 124 580.4

(51) Int. Cl.
*A61B 5/00* (2006.01)
*G16H 50/50* (2018.01)
(Continued)

(52) U.S. Cl.
CPC ............ *A61B 5/4547* (2013.01); *A61B 5/228* (2013.01); *A61C 9/0053* (2013.01);
(Continued)

(58) Field of Classification Search
CPC ..... A61B 5/4547; A61B 5/228; A61C 9/0053; A61C 13/0004; A61C 19/05; G16H 50/50
See application file for complete search history.

(56) References Cited

U.S. PATENT DOCUMENTS 5,131,844 A * 7/1992 Marinaccio ............ A61C 19/04
433/72
5,273,429 A * 12/1993 Rekow ................... A61C 13/00
433/215

(Continued)

FOREIGN PATENT DOCUMENTS

DE  10 2012 214 470 A1  2/2014
DE  10 2016 103 320 A1  8/2017

OTHER PUBLICATIONS

I. A. Venturini P. Poiate et al.: "Three-Dimensional Stress Distribution in the Human Periodontal Ligament in Masticatory, Parafunctional, and Trauma Loads: Finite Element Analysis", Journal of Periodontology, vol. 80, No. 11, pp. 1859-1867 (2009).

*Primary Examiner* — Nicholas D Lucchesi
(74) *Attorney, Agent, or Firm* — Norman B. Thot

(57) ABSTRACT

A method for representing a tooth position under biting forces includes creating first surface data of a portion(s) of a maxilla tooth row and second surface data of an opposing portion(s) of a mandible tooth row, producing a digital surface model from the surface data, creating a data record which includes outer surface data of teeth lying in the portions of the maxilla tooth row and the mandible tooth row in a centric occlusion under biting forces, defining registration regions in the maxilla and mandible in the outer surface data which are not exposed to any force in the centric occlusion, registering the surface data on the outer surface data based on the registration regions, ascertaining movements of individual teeth outside of the registration regions from the outer surface data, transforming the movements (Continued)

ascertained into the surface data, and creating a modified digital surface model under consideration of the movements.

19 Claims, 1 Drawing Sheet

(51) Int. Cl.
    *A61B 5/22*     (2006.01)
    *A61C 9/00*     (2006.01)
    *A61C 13/00*     (2006.01)
    *A61C 19/05*     (2006.01)

(52) U.S. Cl.
    CPC .......... *A61C 13/0004* (2013.01); *A61C 19/05* (2013.01); *G16H 50/50* (2018.01)

(56) References Cited

U.S. PATENT DOCUMENTS

| | | | |
|---|---|---|---|
| 7,716,024 B2 * | 5/2010 | Hultgren | G06T 19/20 703/6 |
| 8,798,346 B2 * | 8/2014 | Cizek | G06T 7/33 382/130 |
| 9,730,779 B2 * | 8/2017 | Kopelman | A61C 5/70 |
| 9,999,487 B2 * | 6/2018 | Kusch | G06T 7/33 |
| 10,059,059 B2 * | 8/2018 | Kopelman | A61C 13/20 |
| 10,123,706 B2 * | 11/2018 | Elbaz | G06T 7/75 |
| 2006/0275736 A1 | 12/2006 | Wen et al. | |
| 2007/0031774 A1 * | 2/2007 | Cinader | A61C 7/00 433/24 |
| 2007/0207441 A1 * | 9/2007 | Lauren | A61C 13/0004 433/213 |
| 2009/0068617 A1 * | 3/2009 | Lauren | A61C 5/77 433/213 |
| 2012/0015316 A1 * | 1/2012 | Sachdeva | A61C 13/0004 433/24 |
| 2013/0325431 A1 * | 12/2013 | See | G06T 19/00 703/11 |
| 2015/0235412 A1 | 8/2015 | Adamson et al. | |
| 2019/0021651 A1 | 1/2019 | Hanssen et al. | |
| 2019/0231490 A1 * | 8/2019 | Sabina | A61B 1/0638 |
| 2020/0268485 A1 * | 8/2020 | Hanssen | A61C 7/002 |

* cited by examiner

METHOD FOR DETERMINING AND VISUALIZING TOOTH POSITIONS UNDER THE ACTION OF BITING FORCES

CROSS REFERENCE TO PRIOR APPLICATIONS

This application is a U.S. National Phase application under 35 U.S.C. § 371 of International Application No. PCT/EP2018/078231, filed on Oct. 16, 2018 and which claims benefit to German Patent Application No. 10 2017 124 580.4, filed on Oct. 20, 2017. The International Application was published in German on Apr. 25, 2019 as WO 2019/076888 A1 under PCT Article 21(2).

FIELD

The present invention relates to a method for representing a tooth position under the action of biting forces. A first record of three-dimensional surface data of at least one portion of the tooth row of the maxilla and a second record of three-dimensional surface data of at least one opposite portion of the tooth row of the mandible are thereby created. These two data records containing three-dimensional surface data are then unified to produce a digital surface model.

BACKGROUND

Such a method is, for example, described in DE 10 2012 214 470 A1. DE 10 2016 103 320 A1 thereby describes a system for intraoral measurement of jaw displacements. Such digital models of the teeth are increasingly used in dentistry for diagnostic purposes and within the scope of producing dental prostheses. A record of the surface data of at least one portion of a tooth row is here captured as a three-dimensional surface model, in particular via a digital intraoral camera. In the case of occlusal appliances and dental prostheses, the contact points or contact areas of the teeth with the corresponding teeth of the opposite jaw and the forces occurring when biting are in particular important and are increasingly becoming a focus of attention.

The prior art has described the use of an intraoral camera to record surface data of the maxilla and of the mandible and then to spatially assign the surface data via a recording of the teeth outer surfaces in the centric occlusion, i.e., via a buccal recording. As a result of the spatial assignment thus ascertained, static contact points and contact areas with the respective teeth in the opposite jaw can be calculated and displayed.

A disadvantage of this procedure is that possible individual movements of the teeth are not taken into account during the assignment of mandible to maxilla via the buccal recording. Individual teeth are moved in their ligaments due to the biting forces acting between the jaws. The muscular forces acting in the jaws, in particular in the mandible, moreover lead to a non-rigid deformation. The assumption of rigid conditions, and consequently rigidity, made in the prior art falsifies the assignment of mandible to maxilla so that the movements of individual teeth upon contact under force and deformations, in particular of the mandible, cannot be correctly predicted. This leads to the contact points on the occlusion surfaces not being able to be ascertained and displayed correctly, so that a dental prothesis can only be produced with reduced quality and fit.

The practice of clamping a sensor film between the teeth of the maxilla and mandible is also known, the sensor foil allowing direct measurements of the contact points and the forces occurring upon biting. A disadvantage is, however, that the measurement error caused by the thickness of the sensor film is greater than the comparatively small amplitude of the tooth movements during biting. The teeth are also not in natural occlusion on account of the thickness of the sensor film. The contact points impinged on the sensor film thus fail to correspond to reality. The automatic assignment of the measured contact points to the individual teeth and tooth surfaces is also not possible. Such an assignment is, however, vital for the production of the dental prothesis because only such an assignment renders identifiable the parts of the tooth geometry that must be removed by abrasion or that must be formed.

A further disadvantage of the sensor film is that it can only measure the forces that are directed perpendicular to the sensor film. The remaining components of the actual force distribution remain unknown. Each individual film must also be compensated or calibrated in order to obtain correct relative or absolute results of the force measurement. A sensor film can also only be used a few times.

SUMMARY

An aspect of the present invention to provide a method that can be implemented in a simple and cost-effective fashion, via which the movements of individual teeth under the action of a biting force during actual biting and the influence of the movements on contact points and contact areas can be ascertained. A further aspect of the present invention is to provide a corresponding system for carrying out the method.

In an embodiment, the present invention provides a method for representing a tooth position under an action of biting forces which includes creating first surface data of at least one portion of a maxilla tooth row and second surface data of at least one opposing portion of a mandible tooth row, producing a digital surface model from the first surface data and the second surface data, creating a data record comprising outer surface data of teeth lying in the portions of the maxilla tooth row and the mandible tooth row in a centric occlusion under the action of biting forces, defining registration regions in the maxilla and in the mandible in the outer surface data, the registration regions not being exposed to an action of any force in the centric occlusion, registering the first surface data and the second surface data on the outer surface data based on the registration regions, ascertaining movements of individual teeth outside of the registration regions from the outer surface data, transforming the movements ascertained into the first surface data and the second data surface, and creating a modified digital surface model which takes the movements into account.

BRIEF DESCRIPTION OF THE DRAWINGS

The present invention is described in greater detail below on the basis of embodiments and of the drawings in which.

DETAILED DESCRIPTION

Figure 1:
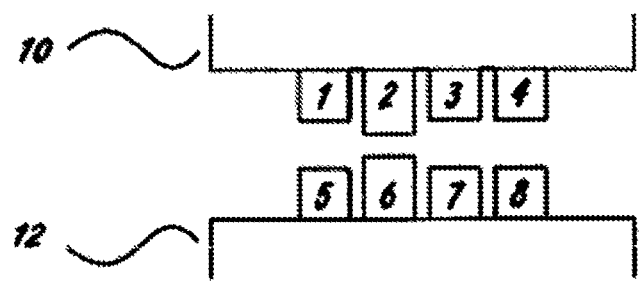
FIG. 1 shows a first step of the surface scans, where the scanned maxilla with its teeth and the scanned mandible with its teeth are shown.

A fundamental aspect of the present invention lies in the fact that a record of likewise three-dimensional outer surface data in the centric occlusion, and consequently under the action of the biting force, is recorded in addition to the two data records containing the three-dimensional surface data of maxilla and mandible, wherein a partial area of the outer surface data is used for the assignment of maxilla and mandible. These outer surface data represent the teeth moved by the action of force. The basic concept now lies in applying the movement of individual teeth inherent to the outer surface data to the surface data of maxilla and mandible and modifying these in accordance with the implemented movement. Using surface data thus modified, it is now possible to create a digital model of the teeth during the centric occlusion under applied forces, from which the actual contact points and contact areas can be ascertained. The surface data of maxilla and mandible can here be taken directly from the patient or from a model taken from the patient, in particular by means of an (intraoral) camera.

A fundamental aspect of the present invention is therefore that at least some of the outer surface data representing the buccal bite, which can be recorded by an intraoral camera, is used for the registration of the available surface data of the maxilla and mandible. The parts of the buccal bite recording that were not deformed by the action of force are here used for the registration. The maxilla and the mandible can thus be brought into the correct spatial position with respect to one another as a whole within a first step. The partial areas of the buccal bite recording whose teeth were deformed by the action of force are now considered in a second step. It is possible to take account of the changes in position of the individual teeth during biting that are caused by forces as a result of the application of such a "non-rigid" transformation. The individual teeth are advantageously segmented in the process so that the teeth can be moved separately from one another in the digital model.

By transferring this deformation inherent to the buccal bite to the individual teeth of the surface model, it is possible to take account of the actual tooth positions and the tooth alignments in the digital model. The actual tooth contacts with the contact areas of the opposite jaw can accordingly be calculated therefrom. An accurately fitting dental prothesis can moreover be produced using the results arising from the procedure according to the present invention.

The present invention provides that the method is implemented so that, initially, the further data record containing the three-dimensional outer surface data of the teeth, which lie in the portions of the tooth rows captured by the surface data, is created in the centric occlusion under the corresponding action of biting forces. Registration regions in the maxilla and in the mandible are then defined in these outer surface data, which registration regions are not exposed to the action of force in the centric occlusion and accordingly are not exposed to any deformation. Since these registration regions are present accordingly in the surface data of the non-deformed maxilla and mandible, they can be used to register these different data records. The first and the second surface data are then registered on the outer surface data on the basis of these registration regions. By comparing structures in the outer surface data and corresponding structures in the surface data, individual teeth that have carried out a movement in the centric occlusion are ascertained outside of the registration regions. These movements are then transformed into the surface data, thereby creating a modified digital surface model of the centric occlusion while taking the movements into account.

An advantage of the procedure according to the present invention lies in the fact that the contact points and contact areas occurring between the teeth can be calculated in a substantially improved fashion over what was ever possible with the previously known methods. A further advantage is that the centric occlusion is not falsified by any sensor film clamped between the teeth. A direct assignment of the contact points to the respective tooth geometry is also possible. Since the position of the contact points on the respective tooth geometry is known, it is possible to determine not only the forces perpendicular to a sensor film but, therebeyond, it is also possible to determine the direction of the force vectors.

In an embodiment of the present invention, successive buccal bites with different biting forces can, for example, be recorded. By taking account of a plurality of buccal records during the registration, it is possible to capture movement sequences of the teeth and ascertain time-varying contact point patterns in realistic fashion. Force calculations can also be fed with the (non-rigid) deformations thus measured. It is, for example, possible to calculate tension forces that the individual tooth movements transfer to the jawbone. It is also possible to calculate forces between a tooth and its periodontal ligament. These forces can then be transferred to the occlusion side, thereby making it possible to determine magnitude and the direction of the force vectors on the occlusion.

The present invention will be described in greater detail below based on the drawings.

The procedure according to the present invention is firstly explained using a first embodiment. The tooth rows of the maxilla and of the mandible of a patient are here initially scanned using an intraoral camera, at least within the scope of the regions of interest, for the purposes of creating the surface data records. Since scanning is carried out in the case of an open mouth or on the jaw regions of a model, no (biting) forces act on the teeth at this time. The individual teeth are advantageously segmented so that they can accordingly be moved separately from one another in the digital model. This allows for non-rigid movements of the individual teeth to be taken into account.

This first step of the surface scans is shown in FIG. 1, where the scanned maxilla 10 with its teeth 1-4 and the scanned mandible 12 with its teeth 5-8 are illustrated. This is the situation in which no forces act on the teeth.

Figure 2:
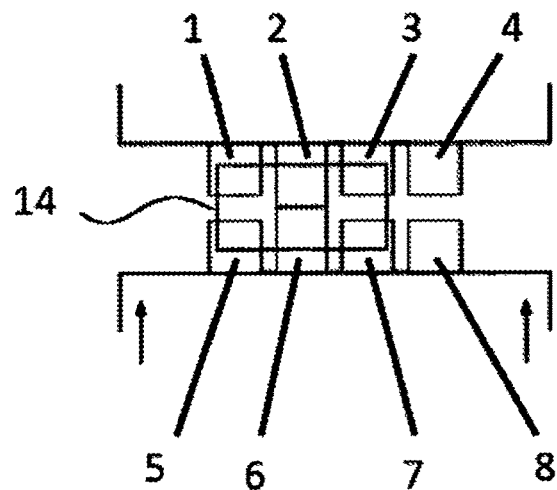
FIG. 2 shows the situation where a patient bites lightly, but where no biting forces yet act on the teeth.

FIG. 2 now shows the situation where the patient bites lightly, but where no biting forces yet act on the teeth. Teeth 2 and 6, however, just come into contact with one another as these are longer than the remaining teeth. The window 14 illustrated using the dashed line elucidates the image section of the intraoral camera, within which the buccal bite can be "seen".

Figure 3:
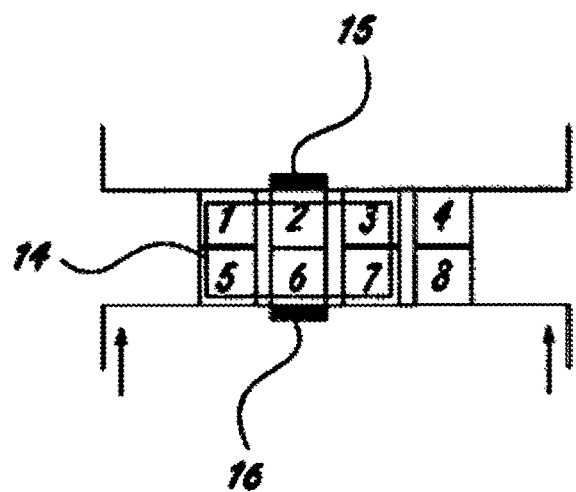
FIG. 3 shows where the patient bites in the centric occlusion, wherein the teeth are displaced in terms of their ligaments or sink on account of the biting forces.

In the next step according to FIG. 3, the patient bites in the centric occlusion, wherein teeth 2 and 6 are displaced in terms of their ligaments or sink on account of the biting forces. The regions 15 and 16 sunk in the ligament are indicated by hatching. In this stage, the actual tooth positions deviate from the positions manifested in the digital model on account of the displacements. Outer surface data, and consequently the buccal bite, are now recorded by an intraoral camera, in particular, in this strong centric occlusion. The non-rigid tooth movements caused by the biting forces are consequently "encrypted" in the buccal bite.

Registration regions identified as such in the buccal bite, which have not had biting forces applied thereto and have therefore not been moved, are now selected, in particular automatically. This selection can be implemented automatically on the basis of a comparison of surface data and outer surface data. Regions identified as being identical in both data records can be used as registration regions. Only portions of the teeth 1, 3, 5 and 7 are thus used for the registration in this case.

On account of the segmentation of the teeth in the digital model, the movements ascertained from the non-rigid buccal bite can now be transferred to the individual teeth in the digital model in a further step. Contact points and contact areas between the teeth that correspond substantially more closely to the actual situation in the mouth of the patient than was the case in the initial rigid digital model can be ascertained in this modified digital model.

In the present example, teeth 2 and 6 are separately registered to the buccal bite recording in the digital model on the basis of the segmentation so that they come to rest perfectly on the buccal bite. How far the teeth 2 and 6 have sunk into the ligaments is hence also known, the corresponding forces can thus be calculated.

In a second embodiment of the present invention, a sequence of states under the changing action of force is recorded within the closing movement. For the purposes of creating a first digital model, the tooth rows of maxilla and mandible of the patient are once again initially scanned with an intraoral camera therefor. The individual teeth are then segmented in the digital model. The intraoral camera is then brought into a position in order to record the buccal bite under the action of the biting force. The patient now carries out a closing movement, with none of the teeth being in contact with their counterparts at the start of the closing movement. During the closing movement, and more particularly following the first contact of the teeth, outer surface data are respectively recorded by the intraoral camera at certain successive times so that buccal recordings are available for a plurality of time steps of the closing sequence under the increased application of force and, accordingly, under changing tooth positions. A plurality of or all teeth are in contact under the biting force at the end of the closing movement sequence.

The registration resorts to a segmentation of the scanned teeth of maxilla and mandible and evaluates the closing sequence as follows.

A buccal bite registration of the maxilla with the mandible is carried out for each time step of the closing sequence. Only the teeth that (still) have no contact with the opposite side, and which accordingly have no force applied thereto, are here used in each time step as registration regions for the buccal bite registration. This provides that the teeth not subject to an elastic deformation (in the ligament) are used for the buccal bite registration. A (rigid) transformation $T_i$, which describes the position of the maxilla in relation to the mandible, is accordingly produced for each time step of the closing sequence. The position of the non-rigid teeth, non-rigid because these are already in contact, is produced by transformation at the time step i, within the scope of which transformation the movements of individual teeth are ascertained from the outer surface data and are transformed as corresponding movements into the surface data. The final position and orientation of a tooth in relation to the opposite jaw, thus ascertained, corresponds to reality with a great accuracy.

The absolute position of mandible in relation to maxilla can be ascertained at any time on the basis of the non-contacting teeth. As a result, it is also possible to indirectly make a statement about the position and the orientation of the jaw joints since the recording of the absolute position of the jaws relative to one another is not falsified by locally displaced teeth. With the registration against the buccal bite, how strongly the respective tooth has sunk into the ligament on account of the action of force can accordingly be ascertained for the contacting teeth. The forces occurring in the ligament moreover arise by calculation when the deformation properties and the material parameters are taken into account, and the forces acting at the contact points of the occlusion arise accordingly.

In a variant of the second embodiment, contact areas and contact forces can be ascertained, even if all teeth are subject to the action of force. The tooth rows of maxilla and mandible are here once again scanned using an intraoral camera for the purposes of creating the three-dimensional surface data records. Regions of the gingiva of maxilla and mandible are also captured using these scans. In this case, the individual teeth are segmented in the digital model together with the gingiva.

In a further step, the intraoral camera is brought into the buccal bite position, whereby the field-of-view of the camera captures not only the teeth, but in this case the teeth with the gingiva of maxilla and mandible. The patient then carries out a closing movement, at the start of which none of the teeth are in contact with the opposite side. All teeth captured by the intraoral camera are in contact under the action of force at the end of the closing movement sequence. All teeth in particular sink into their ligament to a greater or lesser extent. The registration algorithm then resorts to the segmentation and evaluates the closing sequence only using the gingiva of the maxilla and mandible for the registration of the positional relationship. Via the teeth movements in relation to the (stationary) gingiva, it is possible to calculate the forces between all teeth and the ligament by virtue of said forces being calculated from the sinking amplitudes of the teeth in the ligament and the mechanical properties of the ligaments. The occurring forces can, for example, be calculated using a finite element method.

The second embodiment can alternatively be used to ascertain, in absolute values, the actually occurring forces when biting with the aid of a sensor film. A sensor film that allows a measurement of the absolute forces is thereby introduced between the teeth. A closing sequence with the sensor film as a buccal bite sequence is then recorded with an intraoral camera. The segmented individual teeth of the digital tooth model are once again aligned with the buccal bite sequence. The contact points recorded by the film are aligned with the correctly aligned teeth. The same closing sequence is also recorded without sensor film. The registration according to the present invention is applied to the surface model in the case of both closing sequences in order to ascertain the natural tooth positions with and without film.

The forces measured by the sensor film can be transferred to the situation without film with knowledge of the actual centric occlusion without the sensor film. The falsification by the thickness of the sensor film can consequently be removed by calculation. The deformation remaining in the sensor film can be scanned with the intraoral camera following the force measurement. The accuracy of the assignment can be further improved by recording the spatial distortion of the sensor film. The spatial distortion recorded can thus in turn consequently be registered in relation to the tooth geometries and hence the assignment of contact points on the film to contact points on the tooth geometries can be ascertained.

The sensor film can alternatively be mechanically connected to the intraoral camera in a defined manner. The measured contact points can more easily be transferred to the tooth geometries with knowledge of the mechanical coupling between sensor film and intraoral camera because a common coordinate system between the sensor film and the recorded tooth geometries is thereby created.

The sensor film is advantageously printed with a defined pattern that simplifies the assignment between the recorded contact points and the tooth geometries. The assignment is implemented via a part of the pattern also being captured during the buccal bite recording, and the spatial assignment between film and tooth geometries being at least partly known.

Conventional blueprint paper can be used instead of a sensor film. Following the centric occlusion recording with the blueprint paper and the buccal recording, the blueprint paper is recorded by the intraoral camera and the contact points are ascertained from the centric occlusion position. The contact points evident on the blueprint paper are then transferred to the actual tooth geometries. The blueprint color printed on the teeth can moreover be captured by a further scan with the intraoral camera. The assignment between the blueprint points on the paper and the corresponding points is thereby simplified.

It may also be advantageous to mechanically connect the blueprint paper to the intraoral camera in a defined fashion. The measured contact points can be transferred to the tooth geometries more easily with knowledge of the mechanical coupling between blueprint paper and intraoral camera via a common coordinate system being created between contact points on the blueprint paper and the recorded tooth geometries.

Like the above-described sensor film, the blueprint paper can also additionally be printed with a defined pattern.

In an embodiment of the present invention, the position of a tooth calculated in the buccal bite can, for example, be used to calculate the force acting on the tooth, whereby certain teeth are in particular removed from the occlusion when biting by way of records. Such records can be printed on the basis of jaw movement data. It is here also advantageous to manufacture the (printed) records at different angles in order to load certain parts or directions of the periodontal ligament and hence calculate forces.

In an embodiment of the present invention, the at least partly non-rigid transformations can, for example, be transferred to the roots in a fitting tomographic recording of the bone. The forces on the roots and the surrounding tissue can also be calculated.

The present invention is not limited to embodiments described herein; reference should be had to the appended claims.

What is claimed is:

1. A method for representing a tooth position under an action of biting forces, the method comprising:
creating first surface data of at least one portion of a maxilla tooth row and second surface data of at least one opposing portion of a mandible tooth row;
producing a digital surface model from the first surface data and the second surface data;
creating a data record comprising outer surface data of teeth lying in the portions of the maxilla tooth row and the mandible tooth row in a centric occlusion under the action of biting forces of a patient;
defining registration regions in the maxilla and in the mandible in the outer surface data, the registration regions not being exposed to an action of any force in the centric occlusion;
registering the first surface data and the second surface data on the outer surface data based on the registration regions;
ascertaining movements of individual teeth outside of the registration regions from the outer surface data;
transforming the movements ascertained into the first surface data and the second surface data; and
creating a modified digital surface model which takes the movements into account.

2. The method as recited in claim 1, further comprising:
segmenting individual teeth from the first surface data and the second data surface to obtain segmented individual teeth; and
transferring the movements to the modified digital surface model which includes the segmented individual teeth.

3. The method as recited in claim 2, further comprising:
calculating tooth contacts with at least one of contact points, contact areas, contact distances, and contact forces from the modified digital surface model.

4. The method as recited in claim 1, wherein teeth that are not in contact with an opposite tooth are defined as registration regions in the outer surface data.

5. The method as recited in claim 1, further comprising:
defining regions of the gingiva as registration regions in the outer surface data.

6. The method as recited in claim 1, wherein the registration regions are defined automatically using a registration algorithm.

7. The method as recited in claim 1, further comprising:
recording a sequence of states under a changing action of force within a closing movement,
wherein,
the outer surface data is respectively recorded at certain successive times.

8. The method as recited in claim 1, wherein a position of a tooth calculated in a buccal bite is used to calculate a force acting on the tooth.

9. The method as recited in claim 8, wherein certain teeth are excluded from the occlusion when biting by way of records.

10. A system for implementing a method for representing a tooth position under an action of biting forces,
wherein the system comprises:
an intraoral camera; and
a computer,
wherein the method comprises:
creating first surface data of at least one portion of a maxilla tooth row and second surface data of at least one opposing portion of a mandible tooth row via the intraoral camera scanning the maxilla tooth row and the mandible tooth row;
producing a digital surface model from the first surface data and the second surface data with the computer;
creating a data record comprising outer surface data of teeth lying in the portions of the maxilla tooth row and the mandible tooth row in a centric occlusion under the action of biting forces of a patient via the intraoral camera;
defining, via a registration algorithm, registration regions in the maxilla and in the mandible in the outer surface data, the registration regions not being exposed to an action of any force in the centric occlusion;
registering, via the computer, the first surface data and the second surface data on the outer surface data based on the registration regions;
ascertaining, via the computer, movements of individual teeth outside of the registration regions from the outer surface data;

transforming, via the computer, the movements ascertained into the first surface data and the second surface data; and creating, via the computer, a modified digital surface model which takes the movements into account.

11. The system as recited in claim 10, wherein the defining of the registration regions in the maxilla via the registration algorithm is performed by the computer.

12. The system as recited in claim 10, wherein the creating of the data record comprising outer surface data of teeth lying in the portions of the maxilla tooth row and the mandible tooth row in the centric occlusion is performed via the intraoral camera scanning the outer surface of the teeth lying in the portions of the maxilla tooth row and the mandible tooth row in the centric occlusion under the action of the biting forces.

13. The system as recited in claim 10, wherein the method further comprises:

segmenting, via the computer, individual teeth from the first surface data and the second data surface to obtain segmented individual teeth; and transferring, via the computer, the movements to the modified digital surface model which includes the segmented individual teeth.

14. The system as recited in claim 13, wherein the method further comprises:

calculating, via the computer, tooth contacts with at least one of contact points, contact areas, contact distances, and contact forces from the modified digital surface model.

15. The system as recited in claim 10, wherein the method further comprises:

defining, via the computer, teeth that are not in contact with an opposite tooth as registration regions in the outer surface data.

16. The system as recited in claim 10, wherein the method further comprises:

defining, via the computer, regions of the gingiva as registration regions in the outer surface data.

17. The system as recited in claim 10, wherein the method further comprises:

recording, via the intraoral camera, a sequence of states under a changing action of force within a closing movement, wherein, the outer surface data is respectively recorded at certain successive times via the intraoral camera.

18. The system as recited in claim 10, wherein the method further comprises:

using a position of a tooth calculated by the computer in a buccal bite to calculate a force acting on the tooth.

19. The system as recited in claim 18, wherein the method excludes certain teeth from the occlusion when biting by way of records.

* * * * *